United States Patent
Cadours et al.

(10) Patent No.: US 7,759,528 B2
(45) Date of Patent: Jul. 20, 2010

(54) ACETONITRILE REMOVAL FROM THE OLEFINIC FEED OF ETHER PRODUCTION PROCESSES USING IONIC LIQUIDS

(75) Inventors: Renaud Cadours, Francheville (FR); Alain Forestiere, Vernaison (FR); Christophe Vallee, Fontaine (FR)

(73) Assignee: Institut Francais du Petrole, Rueil Malmaison, Cedex (FR)

( * ) Notice: Subject to any disclaimer, the term of this patent is extended or adjusted under 35 U.S.C. 154(b) by 221 days.

(21) Appl. No.: 11/954,108

(22) Filed: Dec. 11, 2007

(65) Prior Publication Data

US 2008/0154068 A1    Jun. 26, 2008

(51) Int. Cl.
C07C 43/00    (2006.01)
C07C 7/10    (2006.01)
C07C 7/00    (2006.01)

(52) U.S. Cl. .................. 568/699; 568/579; 568/697; 568/689; 585/809; 585/833

(58) Field of Classification Search .................. 518/700; 568/579, 697, 699; 585/809, 833, 851, 856, 585/860, 862, 864, 865, 866, 867
See application file for complete search history.

(56) References Cited

U.S. PATENT DOCUMENTS 4,219,678 A * 8/1980 Obenaus et al. ............. 568/697
5,120,881 A    6/1992 Rosenfeld et al.
5,446,231 A * 8/1995 Arganbright et al. ........ 585/802
5,672,772 A    9/1997 Frey et al.
5,684,212 A    11/1997 Patton et al.
2005/0010076 A1    1/2005 Wasserscheid et al.
2005/0090704 A1* 4/2005 Roettger et al. ............. 585/860

FOREIGN PATENT DOCUMENTS

FR    2875235 A1    3/2006
GB    2418926 A *  4/2006
WO    WO 2005/019137 A1    3/2005

* cited by examiner

*Primary Examiner*—Jafar Parsa
*Assistant Examiner*—Yate' K Cutliff
(74) *Attorney, Agent, or Firm*—Millen, White, Zelano & Branigan, P.C.

(57) ABSTRACT

An enhanced ether production process from an olefinic cut containing at least one iso-olefin and from an alcohol comprises a stage of removal of the acetonitrile present in the hydrocarbon feed by liquid-liquid extraction, the extraction solvent being a non-aqueous ionic liquid of general formula $Q^+A^-$, wherein $Q^+$ is an ammonium, phosphonium and/or sulfonium cation, and $A^-$ an anion likely to form a liquid salt with said cation. Advantageously, the method according to the invention generally allows the amount of water at the etherification reactor inlet to be divided by at least two and thus the purity of the ether produced to be improved.

19 Claims, 2 Drawing Sheets

ACETONITRILE REMOVAL FROM THE OLEFINIC FEED OF ETHER PRODUCTION PROCESSES USING IONIC LIQUIDS

FIELD OF THE INVENTION

The invention relates to a method of removing the acetonitrile present in olefinic cuts containing at least one iso-olefin feeding ether production processes using ionic liquids.

BACKGROUND OF THE INVENTION

Fuel ether production processes conventionally consist in adding an alcohol to a branched olefin. An example thereof is the methyl tertiobutyl ether (MTBE) production process wherein methanol is added to isobutene contained, for example, in an isobutane steam cracking or catalytic cracking or dehydrogenation C4 cut. A similar process allows to produce ethyl tertiobutyl ether (ETBE) from ethanol and isobutene, but also various ethers such as isopropyl tertiobutyl ether (IPTBE) from isopropanol and isobutene, tertio amyl methyl ether (TAME) from methanol and isoamylene, from ex fluid catalytic cracking (FCC) or ex steam cracker C5 cuts, or from the n-pentenes balanced isomerization process Isofive, or ethyl tertioamyl ether (ETAE) from ethanol and isoamylene.

In general terms, industrial processes comprise a reaction section in which the ether is produced in the liquid phase, at low temperature, 50° C. for example, by reaction of an olefinic cut containing at least one iso-olefin with a monoalcohol, in the presence of an ion exchange resin type catalyst, in one or more reactors in series.

The etherification reaction is very selective towards the iso-olefins of the C4 cut, but it is carried out with excess alcohol so as to cause the reaction equilibrium to shift to the production of ether. The composition of the C4 cut varies according to its origin, which may be steam cracking, catalytic cracking, as well as isobutane dehydrogenation or tertiobutanol dehydration. It generally contains less than 50 wt. % iso-olefins, the rest of the feed consisting of a mixture of hydrocarbons inert towards the etherification reaction.

The etherification reaction stage is then followed by a separation stage whose goal is to separate the ether fraction formed and the unreactive or unreacted hydrocarbons for later use, and the excess alcohol. This separation section can consist of a fractionation column allowing to collect the ether at the bottom and the hydrocarbon cut at the top of the column. The non-converted alcohol is recovered, mainly from the hydrocarbon cut, and recycled upstream from the reaction section.

The main reaction between the olefin and the alcohol competes with a parallel reaction of addition of water to the olefin. For example, in the case of ETBE production from isobutene and ethanol, this parallel reaction leads to the formation of tertiobutyl alcohol (TBA). It is therefore advisable to minimize the proportion of water in the etherification reactor feed.

Water has three main origins in the process, corresponding to the residual water contents of the alcohol and of the olefinic feed used, and to the water content of the recycled alcohol. In fact, the latter is generally extracted by subjecting the hydrocarbon fraction obtained at the separation section outlet to a water wash. The recycled alcohol then has a high water content. This recycling can provide up to 50% of the water feeding the reaction section. Patent application FR-A-2,900,924 filed by the assignee provides an alternative to water washing the hydrocarbon cut to recover the alcohol. This invention then brings down the problem of the delivery of water in ether production processes to the feeds of the process: the alcohol and the olefinic feed.

The water content of the olefinic cut is linked with the treatments this cut is subjected to upstream from the etherification process. In fact, the olefinic cut has variable acetonitrile contents according to whether it results from steam cracking, FCC, a dehydrogenation or dehydration operation. This content is less than 20 ppm. The presence of this impurity in the olefinic feed involves a high risk of inhibition of the catalyst used, i.e. ion exchange resins.

An irreversible association is observed between the acetonitrile and the catalysts used in etherification reactors. It is therefore essential to carry out operations of removal of the acetonitrile present prior to sending the olefinic feed to the reaction section.

Generally, removal of this impurity is performed by water wash in a section dedicated to this treatment. The drawback of this solution is then the water saturation of the olefinic feed. The amount of water fed by means of this washing represents at least half the water that goes into the process.

In general, any nitrile molecule that enters the etherification reaction section and has therefore escaped capture by the feed washing plant is trapped by the catalyst resins (which thus lose their acid character and therefore their catalytic activity), either in a first pass, or because these nitrites are recycled through recycling of the alcohol as described in patent U.S. Pat. No. 5,352,848.

The implementation of a process using an extraction liquid other than water for acetonitrile extraction generally allows to divide by at least two the amount of water at the etherification reactor inlet.

SUMMARY OF THE INVENTION

The present invention relates to an enhanced process for producing ethers from an olefinic cut containing at least one iso-olefin and from an alcohol comprising, prior to etherification, a stage of removal of the acetonitrile present in the hydrocarbon feed by liquid-liquid extraction, performed in at least one extraction zone, the extraction solvent being a non-aqueous ionic liquid of general formula $Q^+A^-$, wherein $Q^+$ is an ammonium, phosphonium, guanidinium and/or sulfonium cation, and $A^-$ an anion forming a liquid salt with said cation.

Advantageously, the method according to the invention allows to divide by at least two the amount of water at the etherification reactor inlet and thus to limit catalyst deactivation.

DETAILED DESCRIPTION

Figure 1:
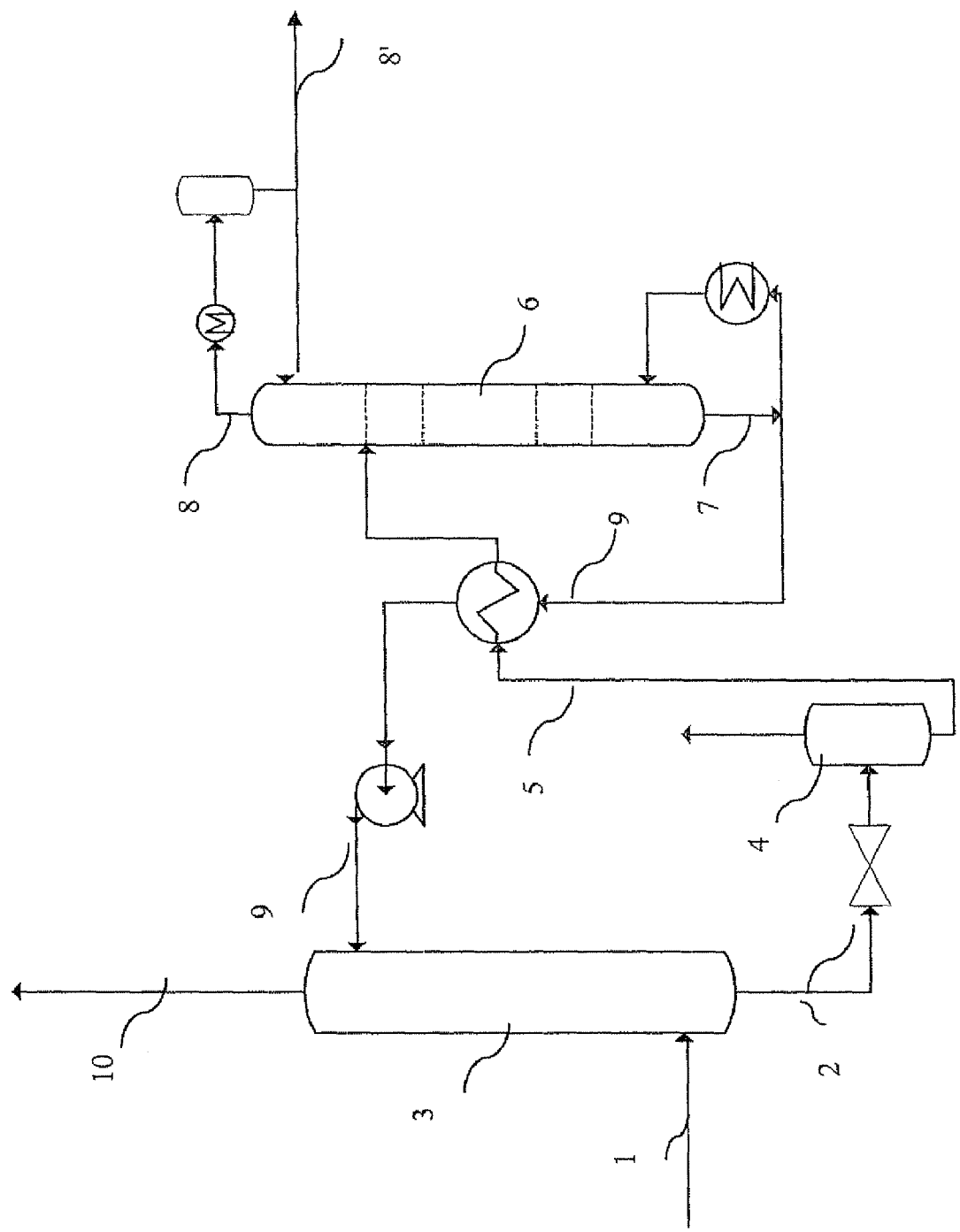
FIG. 1 is a diagram of the method of removing the acetonitrile present in the hydrocarbon feed by means of ionic liquids.

The invention provides an ether production process comprising, prior to etherification, a stage of removal of the acetonitrile present in an olefinic feed containing at least one iso-olefin intended for ether production by liquid-liquid extraction with, as the solvent, a non-aqueous ionic liquid of general formula $Q^+A^-$, wherein $Q^+$ is an ammonium, phosphonium, guanidinium and/or sulfonium cation, and $A^-$ an anion forming a liquid salt with said cation.

This extraction stage takes place prior to the etherification reaction stage carried out in the presence of an ion exchange resin. It therefore allows to very advantageously decrease the amount of water that enters the etherification reactor and, consequently, to limit the hydrolysis reaction of the olefin.

The hydrocarbon feed comprises less than 50 wt. % iso-olefins intended for ether production.

To achieve this extraction, the ionic liquid selected as the solvent is added to the hydrocarbon feed containing approximately 10 to 20 ppm acetonitrile and the assembly is fed into a liquid-liquid extraction column.

By their nature, ionic liquids have no partition coefficient with the hydrocarbon feed, these two entities being immiscible. There is therefore no reason to consider the ionic liquid losses through partition with the feed to be treated. The risk of mechanical entrainment is not limiting either because of the large density difference between the two phases.

These techniques can consist in a cocurrent or counter-current contact of the two liquid phases. One or more mixer settlers or a liquid-liquid contacting column can be used. In this case, it is possible to utilize for example a disk column, a plate column, a pulse column or a packed column (stacked or random packing). To achieve contact between the phases, using a membrane contactor can also be considered. These various techniques can be used alone or in combination. Counter-current techniques are preferably used.

The most suitable separation technique will be selected according to the rules known to the person skilled in the art.

The non-aqueous ionic liquid described in this invention is selected from among the group made up of the liquid salts of general formula $Q^+A^-$, wherein $Q^+$ is an ammonium, phosphonium, guanidinium and/or sulfonium cation, and $A^-$ any anion, organic or inorganic, likely to form a liquid salt at low temperature, i.e. below 100° C. and preferably below 50° C.

In the non-aqueous ionic liquid of formula $Q^+A^-$, the $A^-$ anions are preferably selected from among the following anions: halogenides, nitrate, sulfate, alkylsulfates, phosphate, alkylphosphates, acetate, halogenoacetates, tetrafluoroborate, tetrachloroborate, hexafluorophosphate, trifluoro-tris-(pentafluoroethyl)phosphate, hexafluoroantimonate, fluorosulfonate, alkylsulfonates (methylsulfonate for example), perfluoroalkylsulfonates (trifluoromethylsulfonate for example), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_3^-$, arenesulfonates, possibly substituted by halogen or halogeno-alkyl groups, the tetraphenylborate anion and the tetraphenylborate anions whose aromatic rings are substituted, tetra(trifluoroacetoxy)borate, bis(oxalato)borate, dicyanamide and tricyanomethylide.

The $Q^+$ cations are preferably selected from among the group consisting of phosphonium, ammonium, guanidinium and/or sulfonium. In the formulas hereafter, $R^1$, $R^2$, $R^3$, $R^4$, $R^5$ and $R^6$ each represent hydrogen (except for the $NH_4^+$ cation for $NR^1R^2R^3R^{4+}$), preferably a single substituent representing hydrogen, or hydrocarbyl radicals having 1 to 30 carbon atoms, for example alkyl groups, saturated or non-saturated, cycloalkyls or aromatics, aryls or aralkyls, possibly substituted, comprising 1 to 30 carbon atoms.

$R^1$, $R^2$, $R^3$, $R^4$, $R^5$ and $R^6$ can also represent hydrocarbyl radicals carrying one or more functions selected from among the following functions: —$CO_2R$, —$C(O)R$, —$OR$, —$C(O)NRR'$, —$C(O)N(R)NR'R''$, —$NRR'$, —$SR$, —$S(O)R$, —$S(O)_2R$, —$SO_3R$, —$CN$, —$N(R)P(O)R'R''$, —$PRR'$, —$P(O)RR'$, —$P(OR)(OR')$, —$P(O)(OR)(OR')$, wherein R, R' and R", identical or different, represent each hydrogen or hydrocarbyl radicals having 1 to 30 carbon atoms.

The sulfonium and guanidinium cations preferably meet one of the following general formulas: $SR^1R^2R^{3+}$ or $C(NR^1R^2)(NR^3R^4)(NR^5R^6)^+$, where $R^1$, $R^2$, $R^3$, $R^4$, $R^5$ and $R^6$, identical or different, are defined as above.

The quaternary ammonium and/or phosphonium $Q^+$ cations preferably meet one of the following general formulas: $NR^1R^2R^3R^{4+}$ and $PR^1R^2R^3R^{4+}$, or one of the general formulas: $R^1R^2N=CR^3R^{4+}$ and $R^1R^2P=CR^3R^{4+}$ wherein $R^1$, $R^2$, $R^3$ and $R^4$, identical or different, are defined as above.

The ammonium and/or phosphonium cations can also be derived from nitrogen-containing and/or phosphorus-containing heterocycles comprising 1, 2 or 3 nitrogen and/or phosphorus atoms, of general formulas:

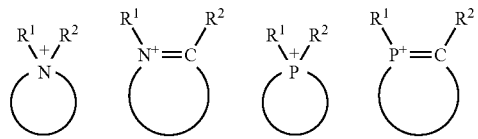

wherein the cycles consist of 4 to 10 atoms, preferably 5 to 6 atoms, and $R^1$ and $R^2$, identical or different, are defined as above.

The quaternary ammonium or phosphonium cation can further meet one of the general formulas as follows: $R^1R^{2+}N=CR^3—R^7—R^3C=N^+R^1R^2$ and $R^1R^{2+}P=CR^3—R^7—R^3C=P^+R^1R^2$, wherein $R^1$, $R^2$ and $R^3$, identical or different, are defined as above, and $R^7$ represents an alkylene or phenylene radical.

Examples of $R^1$, $R^2$, $R^3$ and $R^4$ groups are the following radicals: methyl, ethyl, propyl, isopropyl, primary butyl, secondary butyl, tertiary butyl, butyl, amyl, phenyl or benzyl; $R^7$ can be a methylene, ethylene, propylene or phenylene group.

Preferably, the ammonium and/or phosphonium $Q^+$ cation is selected from among the group consisting of: N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, the (hydroxy-2-ethyl)-1-methyl-3-imidazolium cation, the (carboxy-2-ethyl)-1-methyl-3-imidazolium cation, diethylpyrazolium, N-butyl-N-methylpyrrolidinium, N-butyl-N-methylmorpholinium, trimethylphenyl-ammonium, tetrabutylphosphonium and tributyl-tetradecyl-phosphonium.

Examples of salts that can be used according to the invention are: N-butylpyridinium hexafluorophosphate, trimethylphenylammonium hexafluorophosphate, tetrabutylphosphonium tetrafluoroborate, butyl-3-methyl-1-imidazolium bis(trifluoromethylsulfonyl)amidide, butyl-3-dimethyl-1,2-imidazolium bis(trifluoromethylsulfonyl)amidide, N-butyl-N-methylpyrrolidinium bis(trifluoro-methylsulfonyl)amidide, butyl-3-methyl-1-imidazolium tetrafluoroborate, butyl-3-dimethyl-1,2-imidazolium tetrafluoroborate, ethyl-3-methyl-1-imidazolium tetrafluoro-borate, butyl-3-methyl-1-imidazolium hexafluoroantimonate, butyl-3-methyl-1-imidazolium trifluoroacetate, ethyl-3-methyl-1-imidazolium triflate, (hydroxy-2-ethyl)-1-methyl-3-imidazolium bis(trifluoromethylsulfonyl)amidide, (carboxy-2-ethyl)-1-methyl-3-imidazolium bis(trifluoromethylsulfonyl)amidide and N-butyl-N-methylmorpholinium bis(trifluoromethylsulfonyl)amidide. These salts can be used alone or in admixture.

The description hereafter considers in a non-limitative way a counter-current separation column. In this case, the acetonitrile-laden hydrocarbon feed is fed into the bottom of the column and it is driven upwards. It is thus contacted with the ionic liquid fed at the top of the column. The ionic liquid is thus laden with acetonitrile and the hydrocarbon feed is depleted in acetonitrile.

The mixture collected in the extraction section, at the column bottom, consists of the ionic liquid and of the acetonitrile. It is sent to a section intended for regeneration of the ionic liquid, by distillation and/or expansion for example. The differences between the boiling points of ionic liquids and acetonitrile allows the two compounds to be readily separated.

Advantageously, the ionic liquid is then recycled for extraction.

The purified hydrocarbon feed extracted from the extraction zone and containing less than 0.5 ppm, preferably less than 0.1 ppm acetonitrile, can then be sent to the reaction section without any risk of damaging the ion exchange resins.

The water content decrease allowing to limit the parallel reaction leading for example to the formation of tertiobutyl alcohol (TBA) in the case of ETBE production, the catalytic activity of the resin can thus be increased by at least 20%. It also allows to reduce the required amount of resin or to work at a lower temperature with the same conversion coefficient in the case of an existing unit.

The process for producing ethers from an olefinic feed containing at least one isoolefin and from alcohols according to the invention comprises the following stages:
a) removing the acetonitrile present in the hydrocarbon fraction according to the method described above,
b) mixing the hydrocarbon fraction obtained after stage a) with at least one alcohol stream,
c) etherification reaction by reaction of the mixture obtained in stage b) in the presence of an ion exchange resin so as to obtain an ether-hydrocarbon-alcohol effluent,
d) separating in a fractionation column said ether-hydrocarbon-alcohol effluent into a first effluent enriched in ether and containing part of the excess alcohol and into a second effluent enriched in hydrocarbons containing the other part of the excess alcohol.

The hydrocarbon fraction contains less then 50 wt. % iso-olefins.

The alcohol introduced can be methanol or ethanol.

The present invention is described hereunder in connection with FIG. 1 showing the acetonitrile removal method using ionic liquids (only the main equipments are shown in this figure).

In a non-limitative way, FIG. 1 considers a liquid-liquid counter-current extraction column, by considering in a non-limitative way the use of an ionic liquid of higher density than the hydrocarbon feed.

The hydrocarbon fraction containing olefins and acetonitrile is sent through line (1) to liquid-liquid separation column (3). The ionic liquid is fed into the top of the column through line (9). The circulation in the column takes place in a counter-current flow and the effluent leaving the column through line (2) consists of acetonitrile-laden ionic liquid.

The operating conditions in the extraction section are generally the availability conditions of the hydrocarbon feed, i.e. a pressure of 0.1 to 2 MPa and a temperature of 30° C. to 70° C.

If necessary, a first expansion for salting out the species possibly co-absorbed in the ionic liquid can be carried out in blowdown drum (4). The acetonitrile-laden ionic liquid is then sent through line (5) to a distillation column or an evaporator (6). The operating conditions are determined so as to evaporate the acetonitrile. This operation is generally performed at pressures of 0.1 to 2 MPa, preferably 0.1 to 1 MPa. The column bottom (6) consisting of the ionic liquid is removed through line (7). Line (9) allows the ionic liquid to be sent back to liquid-liquid separation column (3), thus recycling it. At the top of the column, the acetonitrile is collected via line (8) and sent to a treating plant or a conversion plant through line (8').

The hydrocarbon feed containing less than 0.5 ppm, preferably less than 0.1 ppm acetonitrile is extracted from separation column (3) through line (10) and it can be sent to the reaction section of the etherification process.

Figure 2:
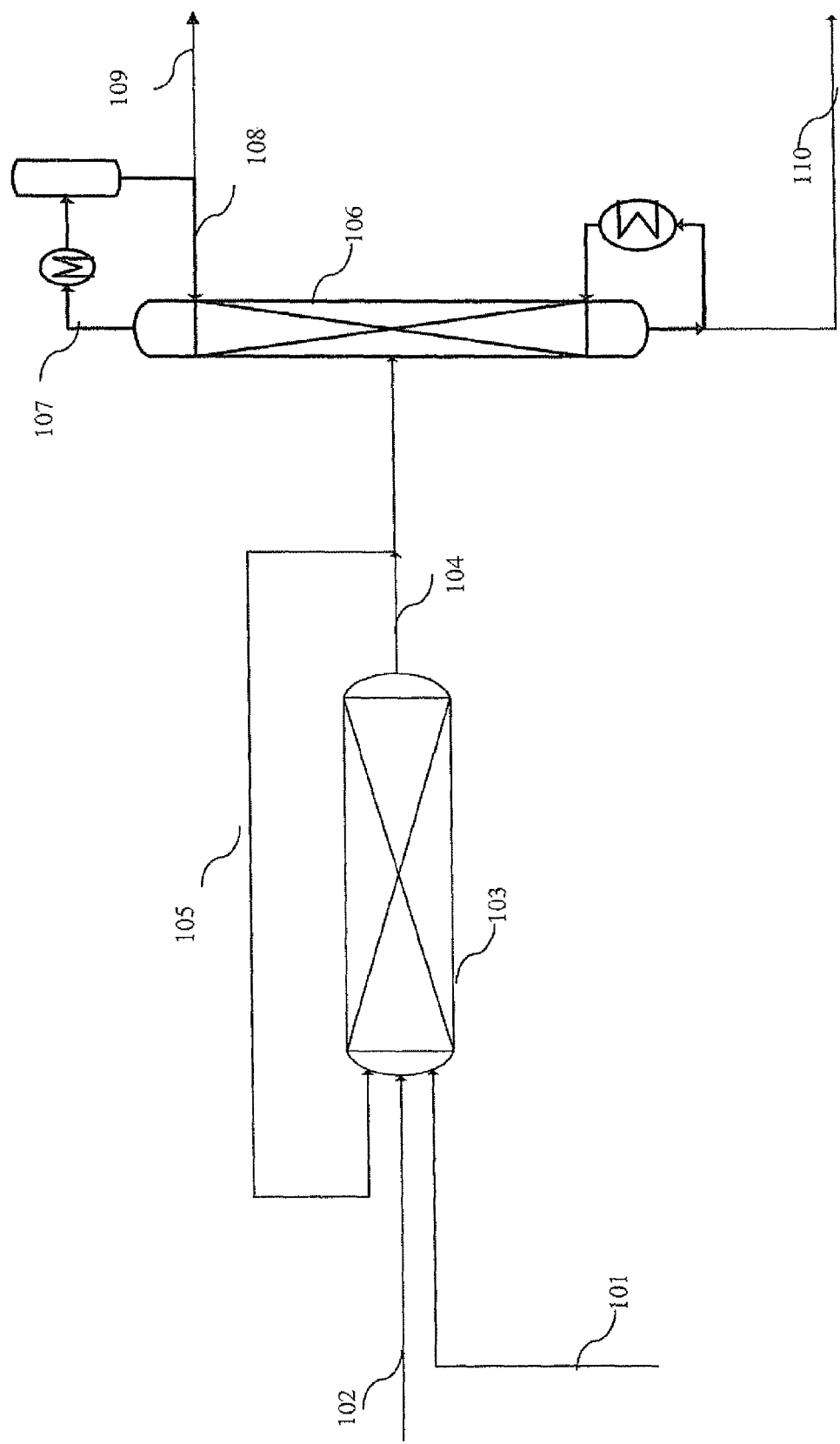
FIG. 2 is a diagram of the process of producing ETBE from isobutene and ethanol, comprising recycling a fraction of the effluent leaving the etherification reactor.

FIG. 2 shows a diagram of the etherification process. A hydrocarbon fraction containing less than 50 wt. % iso-olefin, which has been treated in the acetonitrile removal unit, is fed into etherification reactor (103) through line (101). This hydrocarbon feed is then mixed with the external alcohol source supplied through line (102) and with fraction (105) of the effluent leaving the reactor that is recycled. The effluent leaving the reaction section through line (104) comprises a mixture of unreacted or unreactive hydrocarbons, of ether (reaction product) and of unreacted alcohol. In general, this effluent consists of 10 to 60% ether, 1 to 10% alcohol and 30 to 80% hydrocarbons (molar ratios), its pressure ranges from 0.8 to 2 MPa and its temperature from 50° C. to 90° C.

The liquid effluent from the etherification reactor is then sent to a separation column (106) in order to recover, on the one hand, the ether fraction and, on the other hand, the hydrocarbon-alcohol mixture. Column (106) can be a catalytic column or not, according to whether the fraction is more or less rich in alcohol.

At the top of column (106), a line (107) carries a hydrocarbon gaseous mixture to an exchanger, then to a reflux drum allowing to recover the condensed vapours through line (108) and to discharge the gas fraction through line (109). The mixture discharged at the bottom of column (106) through line (110) essentially comprises the ether phase and alcohol.

The following examples illustrate the invention without any limitative character.

EXAMPLES

Example 1 According To The Invention

Various laboratory tests carried out on a batch basis have allowed to show the efficiency of the alternative solution provided within the scope of the present invention using an ionic liquid instead of water for treating the hydrocarbon feed upstream from the ether production process.

The method of operation for the tests carried out is as follows: 2 ml extraction solvent (ionic liquid or water) and 6 ml feed (a 1000 ppm wt acetonitrile solution in heptane) are stirred for 30 minutes. After 30-minute decantation, 2 g of the upper phase are taken and 200 mg of a standard solution (0.2% toluene solution in heptane) are added, and the mixture is analyzed by gas chromatography. Various ionic liquids were tested and compared with water. The results obtained are given in the table hereafter:

| Extraction solvent | Residual acetonitrile content of the hydrocarbon (ppm wt) after a single partition stage |
|---|---|
| [BMI][CF$_3$SO$_3$] (41 ppm water) | 42 ppm |
| [BMI][PF$_6$] (85 ppm water) | 28 ppm |
| [BMI][PF$_6$] (30 ppm water) | 37 ppm |

-continued

| Extraction solvent | Residual acetonitrile content of the hydrocarbon (ppm wt) after a single partition stage |
|---|---|
| [BMPyrr][NTf2] (20 ppm water) | 82 ppm |
| [BMI][CF$_3$CO$_2$] | 55 ppm |
| H$_2$O | 46 ppm |

[BMI]=butyl-methylimidazolium
[BMPyrr]=butyl-methylpyrrolidinium
[NTf2]=bis(trifluoromethylsulfonyl)imide The ionic liquids tested allow an elimination that is at least as efficient as the water generally used. Their use furthermore affords the advantage of greatly decreasing the water content of the reaction section feed by removing the water present in the hydrocarbon cut. Thus, even for an ionic liquid of lower efficiency than water, the elimination of water delivery for acetonitrile extraction is a significant advantage, notably in relation to the amount of by-products formed.

Example 2

Comparative

On the basis of an ETBE production plant as shown in FIG. 2, a C4 hydrocarbon feed containing 17% by mole of isobutene with a water content of 1500 mole ppm is fed into an etherification reactor operating at 70° C. and 20 bars, at a flow rate of 580 kmol/h with an ethanol feed containing 0.4% water at a flow rate of 113 kmol/h. The water content of this feed is due to the water wash performed in order to obtain a hydrocarbon feed comprising less than 0.5 ppm acetonitrile before it is fed into the reactor. The stream coming from the reactor is divided into two effluents, the first one representing 60% of the stream is recycled to the first reactor at a flow rate of 882 kmol/h in order to optimize the iso-olefin conversion coefficient. The second one is distilled in a column so as to obtain at the column bottom the ether (ETBE) free of hydrocarbons and alcohol.

Subjecting the hydrocarbon feed to a water wash allows to obtain 76.4 mol % ETBE at the distillation column bottom.

Example 3

According To The Invention

Instead of subjecting the hydrocarbon feed to a water wash, the acetonitrile is removed using an ionic liquid. The liquid-liquid separation column is dimensioned with a sufficient number of plates allowing to obtain, after washing, a hydrocarbon feed comprising less than 0.5 ppm acetonitrile.

The fact that no water is fed into the hydrocarbon feed before said feed is sent to the reaction section allows a gain of approximately 2% as regards the purity of the ETBE produced at the bottom of the separation column. With the conditions of example 2, 78.2 mol % ETBE is obtained at the bottom of the distillation column.

The preceding examples can be repeated with similar success by substituting the generically or specifically described reactants and/or operating conditions of this invention for those used in the preceding examples.

The entire disclosures of all applications, patents and publications, cited herein and of corresponding French application No. 06/10974, filed Dec. 12, 2006 are incorporated by reference herein.

From the foregoing description, one skilled in the art can easily ascertain the essential characteristics of this invention and, without departing from the spirit and scope thereof, can make various changes and modifications of the invention to adapt it to various usages and conditions. For example, the invention can be used to remove acetonitrile by the liquid-liquid extraction process of the invention from any organic liquid, for example any hydrocarbon.

The invention claimed is:

1. In a process comprising etherifying an olefinic cut with an alcohol wherein the olefinic cut contains acetonitrile as an impurity, the step prior to etherification comprising a stage a) removal of the acetonitrile present in the olefinic cut by liquid-liquid extraction performed in at least one extraction zone, characterized in that the extraction solvent is a non-aqueous ionic liquid of general formula $Q^{+}A^{-}$, wherein $Q^{+}$ is an ammonium, phosphonium, guanidinium and/or sulfonium cation, and $A^{-}$ an anion forming a liquid salt with said cation.

2. A process as claimed in claim 1, comprising discharging from the extraction zone an acetonitrile-depleted olefinic cut and a mixture consisting essentially of acetonitrile-laden ionic liquid.

3. A process as claimed in claim 2, further comprising passing the mixture discharged from the extraction zone to an ionic liquid regeneration section, and recycling resultant regenerated ionic liquid to the extraction zone.

4. A process as claimed in claim 3, wherein the regeneration of the ionic liquid is performed by distillation and/or expansion.

5. A process as claimed in claim 1, wherein circulation of the olefinic cuts and the extraction solvent in the extraction zone is conducted counter-currently.

6. A process as claimed in claim 1, wherein the $A^{-}$ anion is selected from among groups comprising the following anions: halogenides, nitrate, sulfate, alkylsulfates, phosphate, alkylphosphates, acetate, halogenoacetates, tetrafluoroborate, tetrachloroborate, hexafluorophosphate, trifluoro-tris-(pentafluoroethyl)phosphate, hexafluoroantimonate, fluorosulfonate, alkyl-sulfonates, perfluoroalkylsulfonates, bis(perfluoroalkylsulfonyl)amidides, tris-trifluoromethylsulfonyl methylide of formula $C(CF_3SO_2)_3^{-}$, bis-trifluoromethylsulfonyl methylide of formula $HC(CF_3SO_2)_3^{-}$, arenesulfonates, possibly substituted by halogen or halogeno-alkyl groups, the tetraphenylborate anion and the tetraphenylborate anions whose aromatic rings are substituted, tetra(trifluoroacetoxy)borate, bis(oxalato)borate, dicyanamide and tricyanomethylide.

7. A process as claimed in claim 1, wherein the $Q^{+}$ cation meets one of the following general formulas:

$SR^1R^2R^{3+}$ and $C(NR^1R^2)(NR^3R^4)(NR^5R^6)^{+}$, wherein $R^1$, $R^2$, $R^3$, $R^4$, $R^5$ and $R^6$, identical or different, represent hydrogen (except for the $NH_4^{+}$ cation for $NR^1R^2R^3R^{4+}$), or hydrocarbyl radicals having 1 to 30 carbon atoms.

8. A process as claimed in claim 1, wherein the $Q^{+}$ cation meets one of the following general formulas:

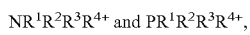

$NR^1R^2R^3R^{4+}$ and $PR^1R^2R^3R^{4+}$, or one of the general formulas:

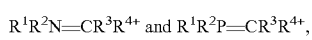

$R^1R^2N=CR^3R^{4+}$ and $R^1R^2P=CR^3R^{4+}$, wherein $R^1$, $R^2$, $R^3$, $R^4$, $R^5$ and $R^6$, identical or different, represent hydrogen (except for the $NH_4^{+}$ cation for $NR^1R^2R^3R^{4+}$), or hydrocarbyl radicals having 1 to 30 carbon atoms.

9. A process as claimed in claim 1, wherein the $Q^{+}$ cation is derived from a nitrogen-containing and/or phosphorus-containing heterocycle comprising 1, 2 or 3 nitrogen and/or phosphorus atoms, the heterocycle comprising 4 to 10 carbon atoms.

10. A process as claimed in claim 1, wherein the $Q^{30}$ cation has one of the general formulas: $R^1R^{2+}N=CR^3—R^7—R^3C=N^+R^1R^2$ and $R^1R^{2+}P=CR^3—R^7—R^3C=P^+R^1R^2$, wherein $R^1$, $R^2$ and $R^3$, identical or different, represent hydrogen or a hydrocarbyl having 1 to 30 carbon atoms, and $R^7$ represents an alkylene or phenylene radical.

11. A process as claimed in claim 7, wherein at least one of groups $R^1$, $R^2$, $R^3$, $R^4$, $R^5$ and $R^6$ carries one or more functions selected from among the following functions: —CO$_2$R, —C(O)R, —OR, —C(O)NRR', —C(O)N(R)NR'R", —NRR', —SR, —S(O)R, —S(O)$_2$R, —SO$_3$R, —CN, —N(R)P(O)R'R', —PRR', —P(O)RR', —P(OR)(OR'), —P(O)(OR)(OR'), wherein R, R' and R", identical or different, represent each hydrogen or hydrocarbyl radicals having 1 to 30 carbon atoms.

12. A process as claimed in claim 1, wherein the $Q^{30}$ cation is selected from the group comprising: N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, the (hydroxy-2-ethyl)-1-methyl-3-imidazolium cation, the (carboxy-2-ethyl)-1-methyl-3-imidazolium cation, diethylpyrazolium, N-butyl-N-methylpyrrolidinium, N-butyl-N-methylmorpholinium, trimethylphenylammonium, tetrabutylphosphonium and tributyl-tetradecyl-phosphonium.

13. A process as claimed in claim 1, wherein the $Q^{30}$ A$^-$ ionic liquid is selected from the group comprising: N-butylpyridinium hexafluorophosphate, trimethylphenylammonium hexafluorophosphate, tetrabutylphosphonium tetrafluoroborate, butyl-3-methyl-1-imidazolium bis(trifluoromethylsulfonyl)amidide, butyl-3-dimethyl-1,2-imidazolium bis(trifluoro-methylsulfonyl)amidide, N-butyl-N-methylpyrrolidinium bis(trifluoro-methylsulfonyl)amidide, butyl-3-methyl-1-imidazolium tetrafluoroborate, butyl-3-dimethyl-1,2-imidazolium tetrafluoroborate, ethyl-3-methyl-1-imidazolium tetrafluoro-borate, butyl-3-methyl-1-imidazolium hexafluoroantimonate, butyl-3-methyl-1-imidazolium trifluoroacetate, ethyl-3-methyl-1-imidazolium triflate, (hydroxy-2-ethyl)-1-methyl-3-imidazolium bis(trifluoromethylsulfonyl)amidide, (carboxy-2-ethyl)-1-methyl-3-imidazolium bis(trifluoromethylsulfonyl)amidide and N-butyl-N-methylmorpholinium bis(trifluoromethylsulfonyl)amidide.

14. A process as claimed in claim 1 comprising, after stage a), the following stages:
   b) mixing the acetonitrile-depleted olefinic cut obtained after stage a) with at least one alcohol stream,
   c) conducting the etherification reaction by reaction of the mixture obtained in stage b) in the presence of an ion exchange resin so as to obtain an ether-hydrocarbon-alcohol effluent,
   d) separating in a fractionation column said ether-hydrocarbon-alcohol effluent into a first effluent enriched in ether and containing part of the excess alcohol and into a second effluent enriched in hydrocarbons containing the other part of the excess alcohol.

15. A process as claimed in claim 1, wherein the olefinic cut comes from a catalytic cracking unit.

16. A process as claimed in claim 1, wherein the olefinic cut comprises less than 50 wt. % iso-olefins.

17. A process as claimed in claim 1, wherein the alcohol is methanol or ethanol.

18. A process according to claim 7, wherein only one of $R^1$, $R^2$, $R^3$, $R^4$, $R^5$ and $R^6$ represents hydrogen.

19. A process according to claim 8, wherein only one of $R^1$, $R^2$, $R^3$, $R^4$, $R^5$ and $R^6$ represents hydrogen.

* * * * *

UNITED STATES PATENT AND TRADEMARK OFFICE
CERTIFICATE OF CORRECTION

PATENT NO. : 7,759,528 B2
APPLICATION NO. : 11/954108
DATED : July 20, 2010
INVENTOR(S) : Cadours et al.

It is certified that error appears in the above-identified patent and that said Letters Patent is hereby corrected as shown below:

Column 9, line 4 reads: "10. A process as claimed in claim 1, wherein the $Q^{30}$ cation"

Should read: --10. A process as claimed in claim 1, wherein the $Q^+$ cation--

Column 9, line 19 reads: "12. A process as claimed in claim 1, wherein the $Q^{30}$ cation"

Should read: --12. A process as claimed in claim 1, wherein the $Q^+$ cation--

Column 9, line 29 reads: "13. A process as claimed in claim 1, wherein the $Q^{30}$ cation"

Should read: --13. A process as claimed in claim 1, wherein the $Q^+$ cation--

Signed and Sealed this

Twelfth Day of October, 2010

David J. Kappos
*Director of the United States Patent and Trademark Office*